(12) United States Patent
Lo et al.

(10) Patent No.: US 7,811,292 B2
(45) Date of Patent: Oct. 12, 2010

(54) SURGICAL INSTRUMENT FOR IMPLANTS

(75) Inventors: Janzen Lo, Allentown, PA (US); Jeffrey C. Wang, Sherman Oaks, CA (US); Chad E Ryshkus, Dover, WI (US)

(73) Assignee: Aesculap Implant Systems, Inc., Center Valley, PA (US)

( * ) Notice: Subject to any disclaimer, the term of this patent is extended or adjusted under 35 U.S.C. 154(b) by 242 days.

(21) Appl. No.: 10/791,447

(22) Filed: Mar. 2, 2004

(65) Prior Publication Data
US 2005/0203538 A1 Sep. 15, 2005

(51) Int. Cl.
*A61B 17/58* (2006.01)
(52) U.S. Cl. .................................. 606/99; 623/17.11
(58) Field of Classification Search ............... 606/86, 606/91, 99, 206, 207; 623/16.11–23.63
See application file for complete search history.

(56) References Cited

U.S. PATENT DOCUMENTS

| | | | | |
|---|---|---|---|---|
| 3,814,102 A | * | 6/1974 | Thal | 606/207 |
| 4,691,903 A | * | 9/1987 | Castille | 269/6 |
| 5,098,437 A | * | 3/1992 | Kashuba et al. | 606/89 |
| 5,122,130 A | * | 6/1992 | Keller | 606/61 |
| 5,171,313 A | * | 12/1992 | Salyer | 606/86 |
| 5,258,007 A | * | 11/1993 | Spetzler et al. | 606/208 |
| 5,391,181 A | * | 2/1995 | Johnson et al. | 606/207 |
| 5,431,658 A | * | 7/1995 | Moskovich | 606/99 |
| 5,522,899 A | * | 6/1996 | Michelson | 606/61 |
| 5,733,290 A | * | 3/1998 | McCue et al. | 606/86 |
| 5,735,857 A | * | 4/1998 | Lane | 606/99 |
| 5,782,830 A | * | 7/1998 | Farris | 606/61 |
| 6,066,174 A | * | 5/2000 | Farris | 606/206 |
| 6,159,215 A | * | 12/2000 | Urbahns et al. | 606/86 |
| 6,440,142 B1 | * | 8/2002 | Ralph et al. | 606/99 |
| 6,663,638 B2 | * | 12/2003 | Ralph et al. | 606/99 |
| 7,278,997 B1 | * | 10/2007 | Mueller et al. | 606/104 |
| 2008/0027552 A1 | * | 1/2008 | Zucherman et al. | 623/17.16 |

* cited by examiner

*Primary Examiner*—Eduardo C Robert
*Assistant Examiner*—Mary Hoffman
(74) *Attorney, Agent, or Firm*—RatnerPrestia

(57) ABSTRACT

An implant insertion device includes a handle, an insertion rod attached to the handle, and an implant gripper attached to the insertion rod. The implant gripper includes a gripping surface that has a movable pin and a fixed pin. The implant insertion device also includes a pin actuator so that the movable pin can be moved into place in an implant. A method of attaching an implant to an implant insertion device is disclosed, as well as a method of detaching an implant from an implant insertion device. Finally, a method of inserting an implant with an implant insertion device is provided.

20 Claims, 9 Drawing Sheets

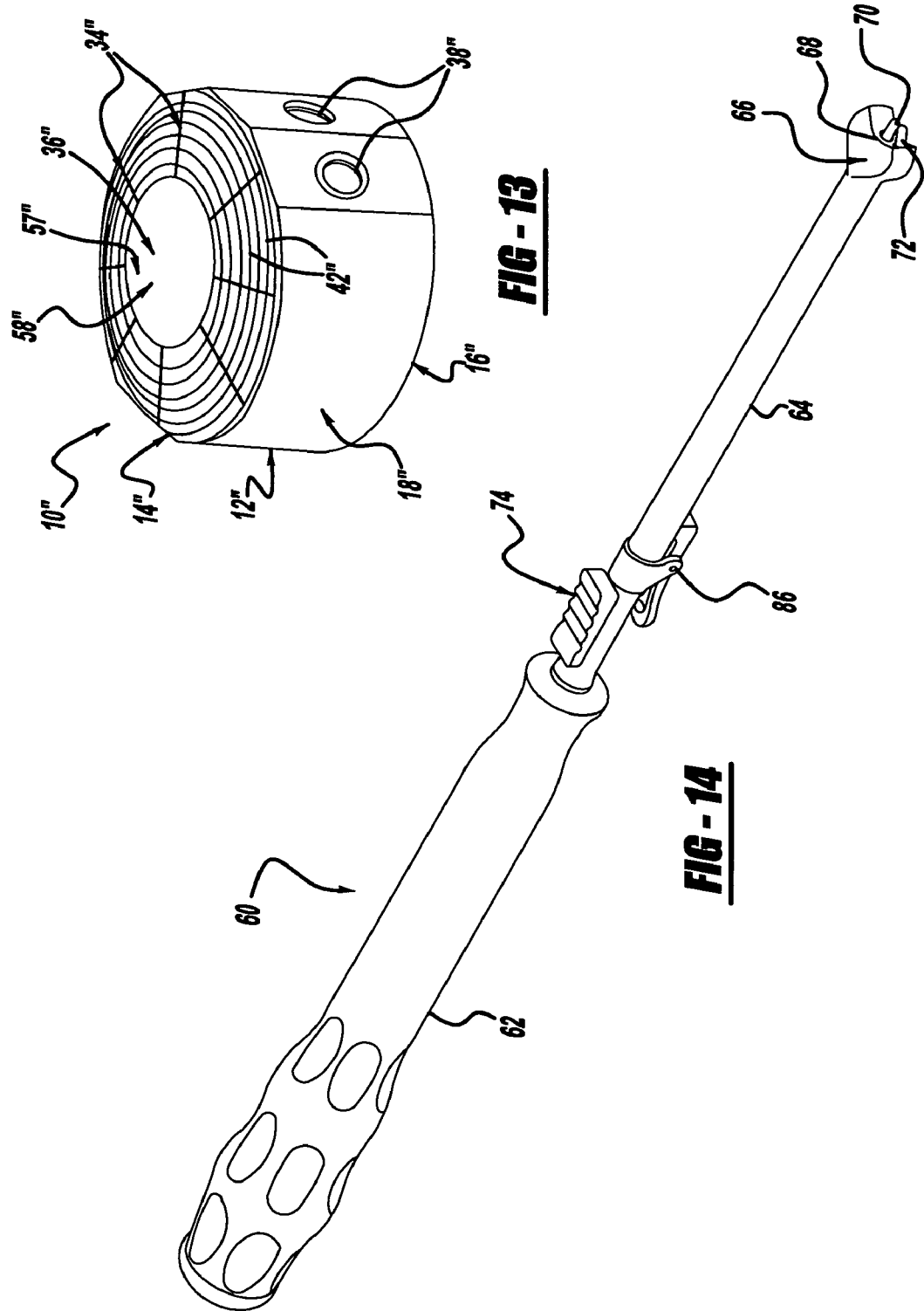

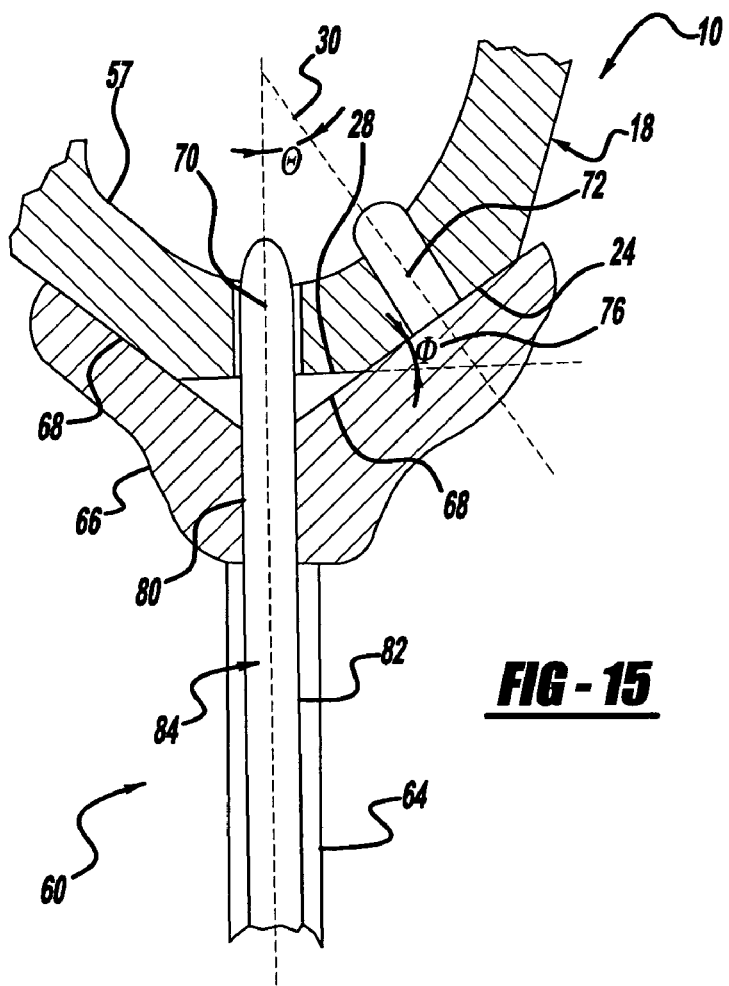
*FIG-15*
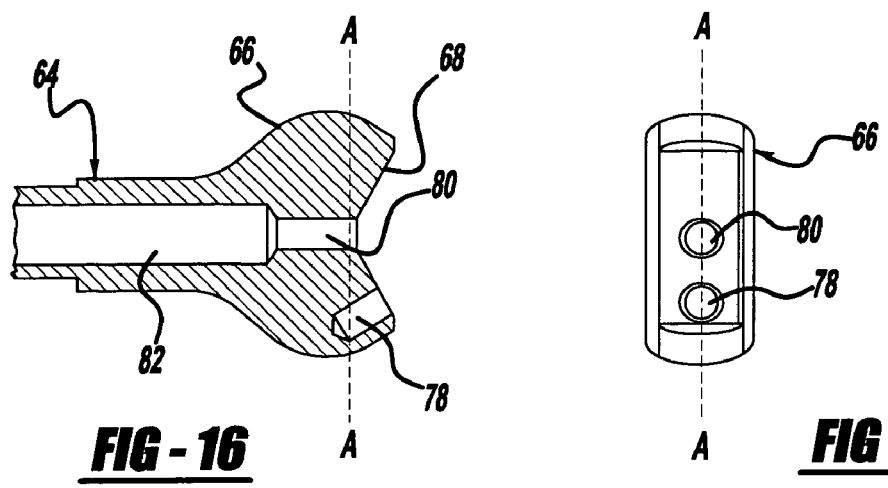
*FIG-16*  *FIG-17*

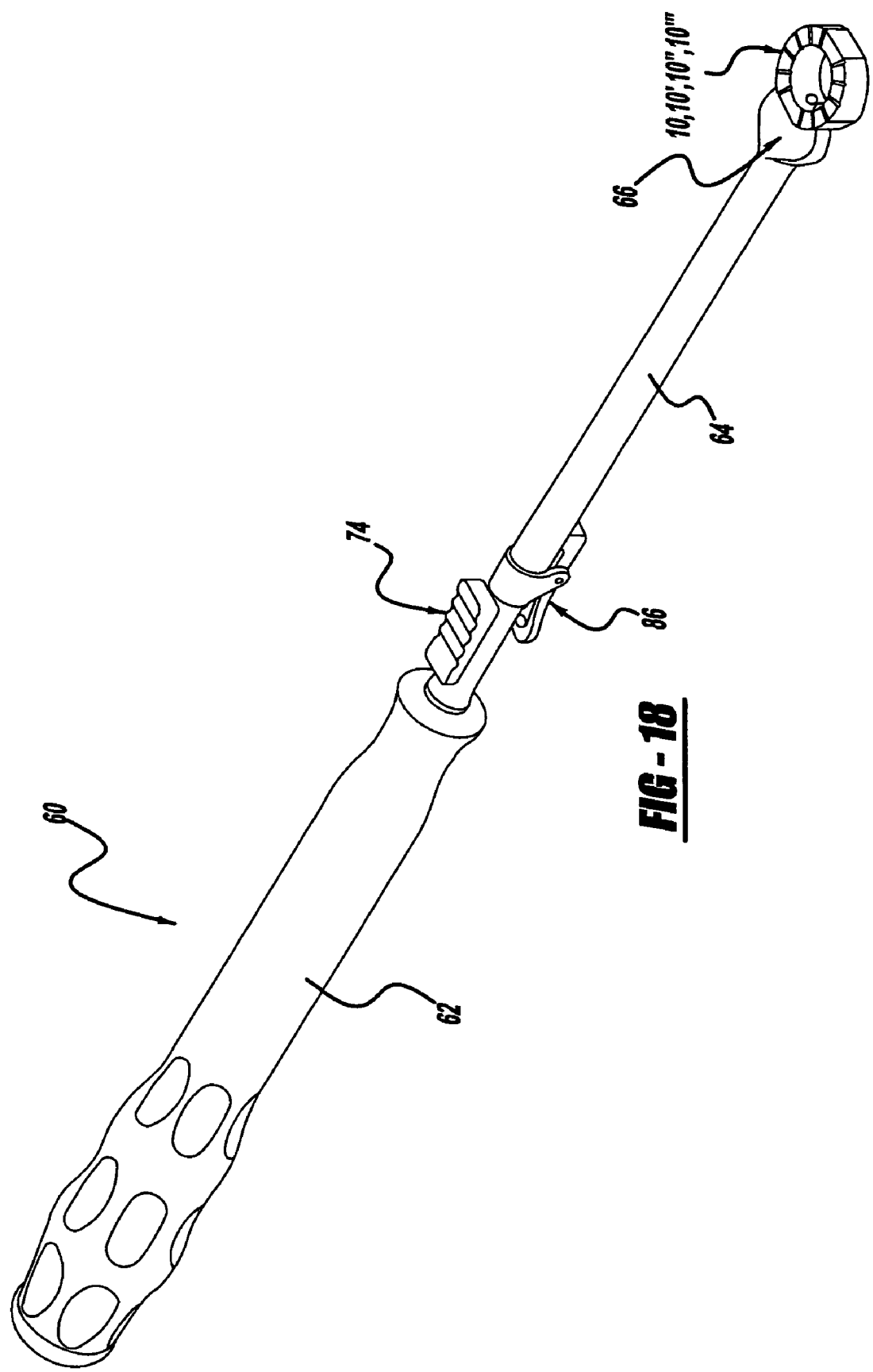

SURGICAL INSTRUMENT FOR IMPLANTS

TECHNICAL FIELD

The present invention relates to a surgical instrument for inserting bone implants between adjacent vertebral bodies of a spinal column. In particular, the present invention relates to an Anterior Lumber Interbody Fusion bone implant insertion device that can be used to insert a bone implant from both a straight anterior direction and an oblique lateral direction.

BACKGROUND

In various orthopedic surgical procedures, it is necessary to secure portions of a spinal column in a relatively fixed relationship. This need is often the result of disease, damage or congenital deformation. For example, when one or more intervertebral disks of the spine degenerate due to trauma or disease, the spinal cord or emergent nerve can become compressed. This condition results in chronic and sometimes debilitating neck, back, or peripheral nerve pain. It has become increasingly recognized that fusion between two adjacent vertebral bodies in the space occupied by the implant is desirable for biomechanical, neurophysiological and anatomical reasons. This "interbody fusion" is biomechanically advantageous because the area to be fused is subjected to compressive loads rather than tensile forces as in the case for posterior element fusions. Biologically, it also has favorable characteristics with a favorable blood supply allowing for graft incorporation and, ultimately, healing. It also offers the best way to restore or maintain the opening of the neuroforamina and to restore or maintain lumbar lordosis. Quite often, spinal deformity correction cannot adequately be performed without interbody surgery. The goals of interbody fusion are (1) to maintain sagittal and frontal plane alignment, (2) to maintain or restore intervertebral space dimension, and (3) to achieve a solid fusion. A number of surgical techniques and graft materials have been utilized to attain a safe and successful pain relieving fusion.

Implants are used to form supports for interbody fusions, whereby, after at least a partial removal of an intervertebral disc and preparation of the roof plates of the vertebrae, the implant that is to be inserted between adjacent vertebrae is introduced into the intervertebral disc space, and it is ensured that the normal gap between adjacent vertebral bodies is reestablished. By forming the cover surfaces facing the adjacent vertebrae with a porous surface or providing them with a profiled structure, the allograft arrangement will become firmly anchored after the implant has been inserted due to growth of the bones of the adjacent vertebrae onto the cover surfaces of the implant. In addition, or as an alternative, at least one break-through or recess in the cover surface of such an implant may be filled with a bone graft substitute or biological bone material before being inserted so that the bone mass accommodated in the implant will be urged to knit with the material of the immediately adjacent vertebrae after the implant has been inserted. A successful fusion stabilizes the spine, reduces pressure on the spinal cord and nerve roots, and reduces or eliminates back pain.

Implants having substantially cylindrical contours are known, for which reference may be made to EP-A 0 369 603 or DE-C 36 37 314 for example. Such types of cylindrical or tube-shaped implants may be additionally provided with a thread-like outer contour in order to enable them to be screwed between the vertebrae by means of a self-threading action. The particular disadvantage of tube-shaped implants of this type, whereby two implants must be used between each two adjacent vertebrae in normal circumstances, is that the implants do not have a defined substantially flat support area on the vertebrate thus giving rise to the fear that difficulties will possibly be encountered in regard to the growth of the incorporated bony material. This can result in implant subsidence and failure. Biomechanically, these threaded devices can cause damage to the implants which compromise the stability of the construct.

Implants have been made out of various materials from bone grafts such as bovine zenograft and allograft tibia, fibula, femur, iliac crest and autograft iliac crest. Threaded cylindrical "cages" made from either titanium or fresh frozen allograft femoral diaphysis have been used as implants. The stability provided by the threaded design allowed these implants to be used as a "stand alone" device not requiring further stabilization. However, there have been increasing reports of non-union when initially fusion was thought to have occurred and subsidence with sinking of the implants into the vertebral body. These cages require tapping in order to be inserted in the spinal column. Tapping causes destruction of the supportive end plates of the vertebrae allowing subsidence or "sinking in" of the implant into the body of the vertebrae. This causes a loss of height of the spinal column with a narrowing of the foramina and a potential compression of the existing nerve root. There is also a flattening of the lumbar lordosis resulting in lower back pain. Therefore, there is a need for an implant that is easy to insert while preserving the endplates for support of the construct.

LifeNet, a developer of allografts and a tissue bank organization, produces an ALIF implant in its Vertigraft® line of bone wedges and shafts for anterior spinal column support. It has a textured surface for increased stability and resistance to graft migration. However, there are also grooves cut in the top and the bottom of the implant so that an insertion instrument can grip the implant. The presence of these grooves reduces the contact area that the implant can have with the adjacent vertebrae. This in turn reduces the compressive strength of the implant. Therefore, there is a need for an implant with an improved contact area while maintaining a way to grip the implant for insertion in the spine.

One surgical tool that is used in the insertion of implants is a pliers-action implant holder. This allows for impaction of the implant, but poor control of rotation, angulations, and does not allow for fine adjustments while the implant is being seated. Insertion using a poor grasping tool typically allows rotation or lateral displacement of the graft before the surgeon has a chance to make final placement and secure it. Another feature lacking in surgical instruments is the ability to remove the instruments in a way which will not encourage side loosening. When an inserted instrument becomes jammed, lateral movement or force will tend to damage the surrounding areas. The surgeon's lack of control over exit angle as well as entry angle is a problem in performing this type of procedure. This is especially complicated by the fact that major blood vessels lie to either side of the operative area. Therefore, there is a need for an implant insertion device that can be removed from the implant with ease and without damage to the implant and surrounding tissues.

Proper surgical tools should lend themselves for automatic adaptation for patients of different size and of different complications. Therefore, there is a need for an implant insertion device that can accommodate various sizes and conditions of patients.

Implants are typically designed to be inserted from an anterior, posterior, or lateral approach. However, such implants are often designed for insertion only from one of the particular approaches of the spine. This is particularly true where implants are intended to maintain non-parallel angulation between the adjacent vertebrae. Therefore, multiple implants each designed for insertion from one of the various approaches to the spine must be maintained in inventory to accommodate the various surgical demands of each procedure. Maintaining multiple implant designs may create inventory problems for both manufacturers and their customers. Moreover, the complications of creating multiple implants to accomplish the same desired spacing is compounded when implants are made of a scarce resource, such as allograft bone. Therefore, there is a need for a spinal implant capable of being inserted in the body from multiple approaches so that the inventory of implants needed can be reduced and so that bone resources can be optimized. An inserter device designed for this specialized implant is also needed.

It is the objective of the present invention to provide an implant insertion device that can accommodate various sizes of bone implants. It is also an objective to provide an implant insertion device that is capable of inserting a bone implant with ease from both the anterior and oblique directions.

SUMMARY OF THE INVENTION

The present invention provides an implant insertion device including a handle, an insertion rod attached to the handle, and an implant gripper attached to the insertion rod. The implant gripper includes a gripping surface that has a movable pin and a fixed pin. The implant insertion device also includes a pin actuator so that the movable pin can be moved into place in a bone implant.

A method of attaching a bone implant to an implant insertion device is provided by first inserting a fixed pin of an implant gripper into an insertion pin hole of the bone implant. Next, a movable pin of the implant gripper is inserted into a second insertion pin hole of the bone implant.

A method is provided of detaching a bone implant from an implant insertion device by first detaching a movable pin of an implant gripper from an insertion pin hole of the bone implant. Next, a fixed pin of the implant gripper is detached from a second insertion pin hole of the bone implant.

Finally, a method of inserting a bone implant with an implant insertion device is provided by first attaching a bone implant to an implant insertion device by inserting a fixed pin of an implant gripper into an insertion pin hole of the bone implant, and inserting a movable pin of the implant gripper into a second insertion pin hole of the bone implant. Next, the bone implant is inserted in a spinal column. Finally, the bone implant is detached from the implant insertion device by detaching the movable pin of the implant gripper from the second insertion pin hole of the bone implant, and detaching the fixed pin of the implant gripper from the insertion pin hole of the bone implant.

BRIEF DESCRIPTION ON THE DRAWINGS

Other advantages of the present invention will be readily appreciated as the same becomes better understood by reference to the following detailed description when considered in connection with the accompanying drawings wherein:

FIG. 13 is a perspective view of a third embodiment of an implant showing radial cuts on the superior and inferior surfaces and counter bore cuts in pin insertion holes;

FIG. 14 is a perspective view of a preferred embodiment of the present invention of an implant insertion device;

FIG. 15 is a close-up view of the present invention of an implant insertion device showing an implant attached to the implant gripper where a fixed pin and movable pin are at an angle of 30 degrees to each other;

FIG. 16 is a cross-sectional view of the present invention of an implant gripper and insertion rod showing pin slots and a shaft to hold a pin driver;

FIG. 17 is a cross-sectional view taken along line A-A in FIG. 16 showing pin slots of the implant gripper.

FIG. 18 is a perspective view of a preferred embodiment of the present invention of the implant insertion device attached to an implant;

DETAILED DESCRIPTION

The present invention provides a new and improved implant insertion device for use in inserting Anterior Lumbar Interbody Fusion (ALIF) bone implants between adjacent vertebrae of a spinal column. It is particularly useful in inserting bone implants from either a straight anterior direction or an oblique lateral direction.

Regarding the present invention, the term "tiered" means having a series of rows or surfaces placed one above another so that each row or surface is not located in the same plane.

The term "osteogenesis" is the formation and growth of bony tissue.

The term "allograft" means a graft of tissue taken from a donor species and grafted into a recipient of an allogenic species, meaning that the donor and recipient are individuals of the same species that are sufficiently unlike genetically to interact antigenically.

The term "concentric" means having a common center. The concentric cuts of the present invention can be all in the same plane, or they can be tiered so that each cut is in a different plane.

Like structure among the several defined embodiments are indicated by primed numbers.

Figure 1:
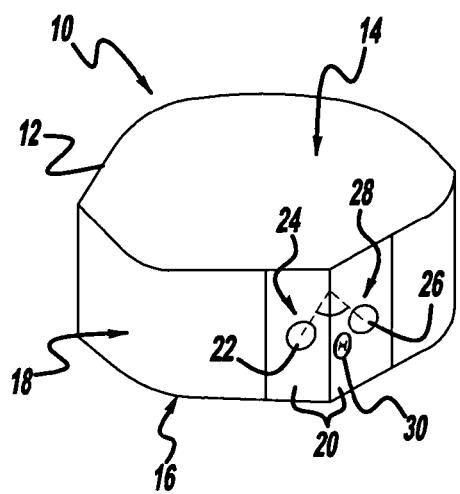
FIG. 1 is a perspective view of a first embodiment of an implant showing an implant with a 30 degree angle between pin insertion holes.

A disk-shaped bone implant used for insertion by an implant insertion device 60 of the present invention is shown generally at 10 in FIG. 1. A bone implant body 12 includes a superior end face 14 and an inferior end face 16. An outer sidewall 18 extends between the superior end face 14 and the inferior end face 16, and includes at least two flat sidewall portions, each indicated at 20. A first insertion pin hole 22 is included on a first flat sidewall portion 24, and a second insertion pin hole 26 is included on a second flat sidewall portion 28. The first insertion pin hole 22 makes an angle theta 30 of about 30 degrees with the second insertion pin hole 26.

Figure 2:
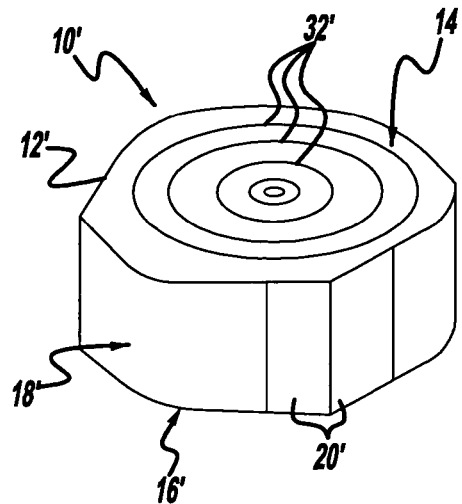
FIG. 2 is a perspective view of a second embodiment of an implant showing concentric cuts.

A second embodiment of an implant used for insertion by the implant insertion device 60 of the present invention is a disk-shaped bone implant shown generally at 10' in FIG. 2. The bone implant body 12' includes a superior end face 14' and an inferior end face 16'. An outer sidewall 18' extend between the superior end face 14' and the inferior end face 16', and includes at least two flat sidewall portions, each indicated at 20'. The superior end face 14' and the inferior end face 16' each include concentric cuts 32'.

Figure 3:
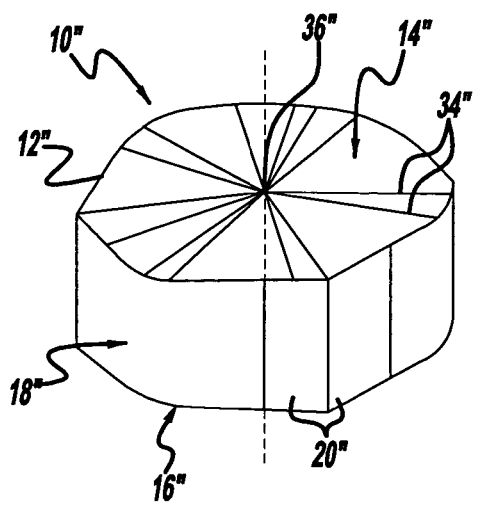
FIG. 3 is a perspective view of a third embodiment of an implant showing radial cuts.

A third embodiment of an implant used for insertion by the implant insertion device 60 of the present invention is a disk-shaped bone implant shown generally at 10" in FIG. 3. The bone implant body 12" includes a superior end face 14" and an inferior end face 16". An outer sidewall 18" extend between the superior end face 14" and the inferior end face 16", and includes at least two flat sidewall portions, each indicated at 20". The superior end face 14" and the inferior end face 16" each include radial cuts 34" extending radially from the outer sidewall 18" to a center 36" of the implant body 12".

Figure 4:
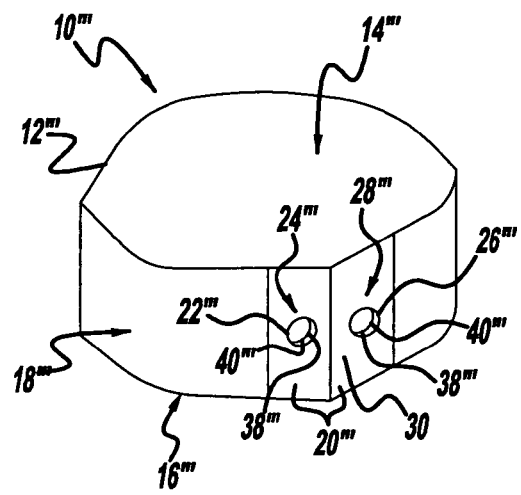
FIG. 4 is a perspective view of a fourth embodiment of an implant showing counter bore cuts inside the insertion pin holes.

A fourth embodiment of an implant used for insertion by the implant insertion device 60 of the present invention is a disk-shaped bone implant shown generally at 10''' in FIG. 4. A bone implant body 12''' includes a superior end face 14''' and an inferior end face 16'''. An outer sidewall 18''' extends between the superior end face 14''' and the inferior end face 16''', and includes at least two flat sidewall portions, each indicated at 20'''. A first insertion pin hole 22''' is included on a first flat sidewall portion 24''', and a second insertion pin hole 26''' is included on a second flat sidewall portion 28'''. A stress reliever in the form of a counter bore cut 38''' is inside a distal end portion 40''' of the pin holes 22''' and 26''' that relieves stress applied by a pin disposed in the pin hole.

A method of forming a bone implant includes cutting concentric cuts 32, 32', 32" into the superior end face 14, 14', 14" and the inferior end face 16, 16', 16" of the bone implant 10, 10', 10". Another method of forming a bone implant 10, 10" includes cutting radial cuts 34, 34" into the superior end face 14, 14" and the inferior end face 16, 16" of the implant 10, 10". Yet another method of forming a bone implant 10, 10" includes cutting concentric cuts 32, 32" into the superior end face 14, 14" and the inferior end face 16, 16" of the bone implant 10, 10", and then cutting radial cuts 34, 34" into the superior end face 14, 14" and the inferior end face 16, 16" of the bone implant 10, 10". In other words, these methods are not mutually exclusive, and can be performed sequentially by hand or by an automated process known in the art. The final shapes can be preformed, cut, or otherwise machined by methods known in the art.

The bone implant 10, 10', 10", 10''' is made out of biocompatible materials. Whenever a foreign object is placed inside the body, rejection reactions can occur ranging from mild to severe irritation and inflammation, and even death. To keep rejection minimal, implants must be biocompatible. Preferably, the bone implant 10, 10', 10", 10''' is made from bone allografts from donor vertebrae bodies. Allografts can be made from cancellous or cortical bone. In order to promote healing of the implant to the vertebral bodies, the implant material should ideally be osteogenic, osteoconductive, osteoinductive, and also be mechanically stable and disease free. Osteogenesis can be induced by including fresh autologous bone marrow cells in bone graft material applied to the bone implant 10, 10', 10", 10'''. A coating of growth factors can also be applied to the bone implant 10, 10', 10", 10''' to promote growth and fusion between the adjacent vertebrae. The bone implant 10, 10', 10", 10''' can also be made of demineralized bone matrix (DBM), carbon fibers, or ceramics. Metals may also be used, although they are capable of sustaining higher stresses than the surrounding bone in the vertebrae and can cause stress-shielding. Optionally, polymers such as high performance thermoplastics may be used. High performance thermoplastics have an elasticity modulus close to that of cortical bone and offer a better post-operative evaluation than some other materials due to their inherent radiolucency. Solid or porous materials can be used, with the advantage of porous materials allowing for enhanced fusion and bone growth between the implant 10 and adjacent vertebrae. Any other suitable biocompatible material can also be used.

The bone implant 10, 10', 10", 10''' is of a diameter and a height to be placed in an appropriate place in the spinal column. Preferably, the diameter is similar to that of the adjacent vertebrae of a patient. Any other suitable diameter can be used. Preferably, the bone implant 10, 10', 10", 10''' is between 7 mm and 22 mm in height. The bone implant 10, 10', 10", 10''' can be produced with a height of 7, 9, 11, 13, 15, 17, 19, or 21 mm depending on the size required to fit between vertebrae. Alternatively, the bone implant 10, 10', 10", 10''' can also be produced with a height of 8, 10, 12, 14, 16, 18, 20, or 22 mm. Any other height that is required for a spinal column can also be used. It is generally in a round, disk-like shape. Other shapes are also suitable, such as the shape of natural bone.

The bone implant 10, 10', 10", 10''' is used to replace broken or damaged vertebrae in a spinal column. The bone implant 10, 10', 10", 10''' is intended to provide support to the spinal column and fuse to adjacent vertebrae. Preferably, the bone implant 10, 10', 10", 10''' is inserted in a spinal column from an oblique lateral direction for fusion in discs between L1 and L5, or the bone implant 10, 10', 10", 10''' is inserted from a straight anterior direction for fusion in discs between L5 and S1. Alternatively, using a suitable size and shape, bone implant 10, 10', 10", 10''' can be inserted in any place desired in the spinal column. The bone implant 10, 10', 10", 10''' is not limited to use in a spinal column, and can be used in any other suitable site in the body.

Figure 5:
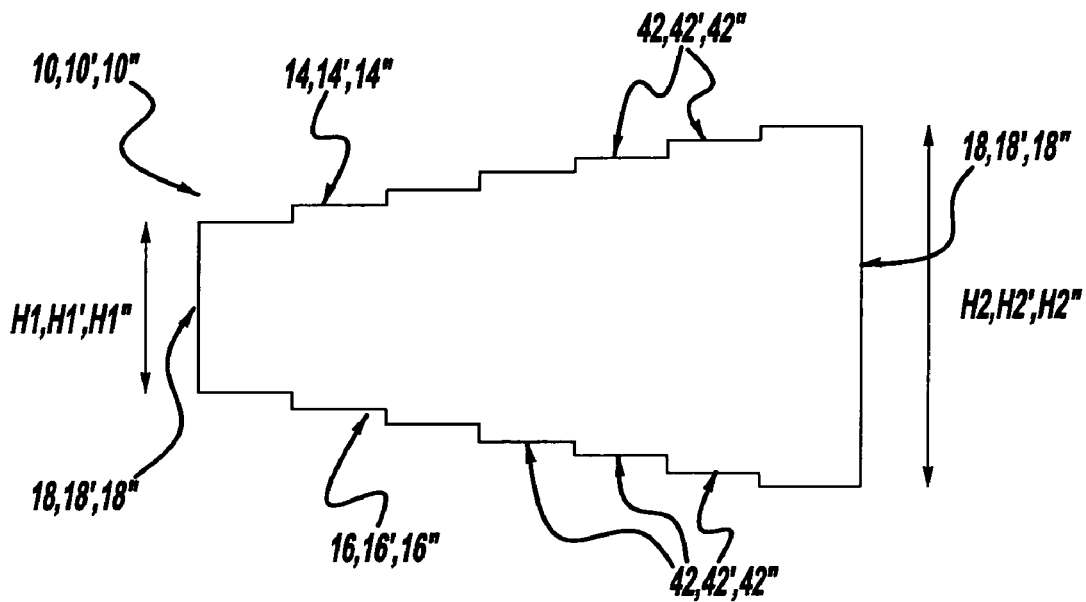
FIG. 5 is a side view of the first, second, and third embodiments of an implant showing tapered superior and inferior end faces.
Figure 6:
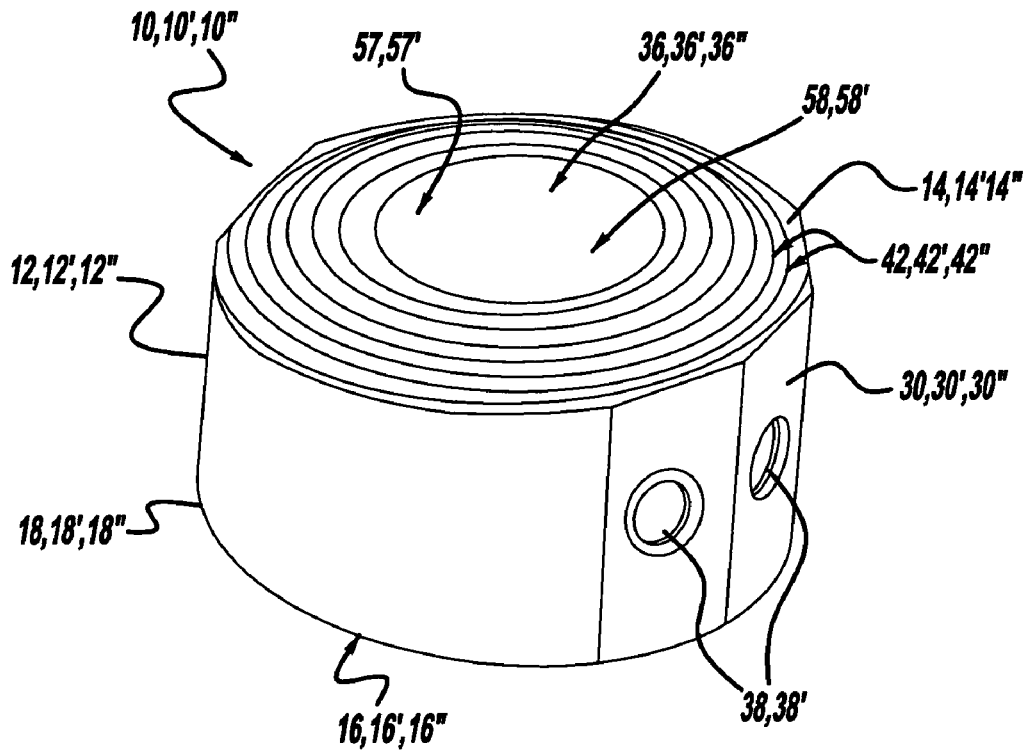
FIG. 6 is a perspective view of a first and second embodiment of an implant showing oval shaped concentric cuts, an inner core, and counter bore holes of the implant.
Figure 7:
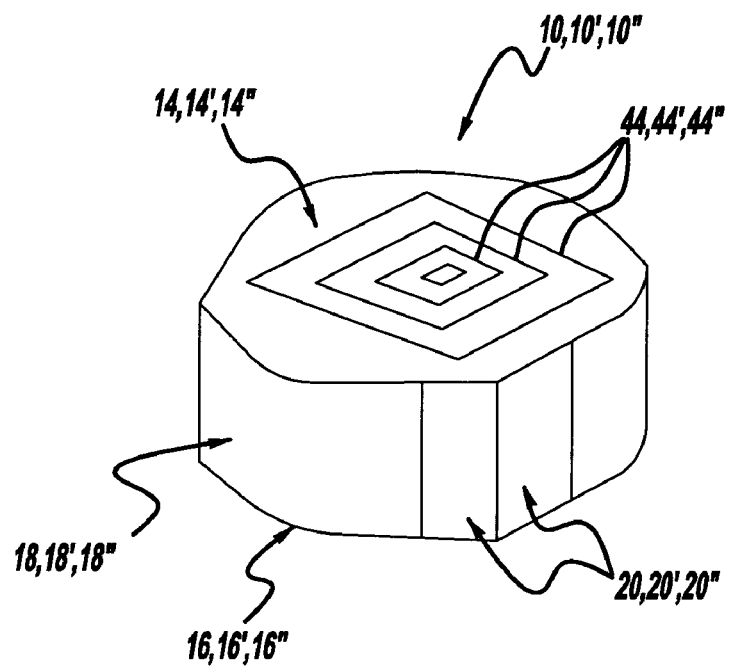
FIG. 7 is a perspective view of an implant showing rectangular concentric cuts.

The bone implant 10, 10', 10", 10''' includes a superior end face 14, 14', 14", 14''' and an inferior end face 16, 16', 16", 16''' on the bone implant body 12, 12', 12", 12'''. The superior end face 14, 14', 14", 14''' and the inferior end face 16, 16', 16", 16''' can be generally parallel to each other, as in FIG. 1. Alternatively, as shown in FIG. 5, in the first, second, and third embodiments, the superior end face 14, 14', 14" and the inferior end face 16, 16', 16" can be tapered from a first height H1, H1', H1" of the outer sidewall 18, 18', 18" to a second height H2, H2', H2" of the outer sidewall 18, 18', 18". In accordance with the second embodiment shown in FIG. 2, the superior end face 14' and the inferior end face 16' include concentric cuts 32'. The superior end face 14, 14', 14" and the inferior end face 16, 16', 16" preferably have tiered concentric cuts 42, 42', 42" extending outwards from a center 36, 36', 36" of the bone implant body 12, 12', 12" to the outer sidewall 18, 18', 18" as shown FIG. 6. The tiered concentric cuts 42, 42', 42" can tier downwards from the center 36, 36', 36" to the outer sidewall 18, 18', 18", or they can tier upwards from the center 36, 36', 36" to the outer sidewall 18, 18', 18". These tiered concentric cuts 42, 42', 42" can be in any shape such as an oval or the rectangular tiered concentric cuts 44, 44', 44" as shown in FIG. 7. The tiered concentric cuts 42, 42', 42" can be cut by cutting means. When the bone implant 10, 10', 10" is made from bone, the tiered concentric cuts 42, 42', 42" can be cut with bone cutting tools. Computer aided modeling can assist in the design and fabrication of the tiered concentric cuts 42, 42', 34".

Figure 8:
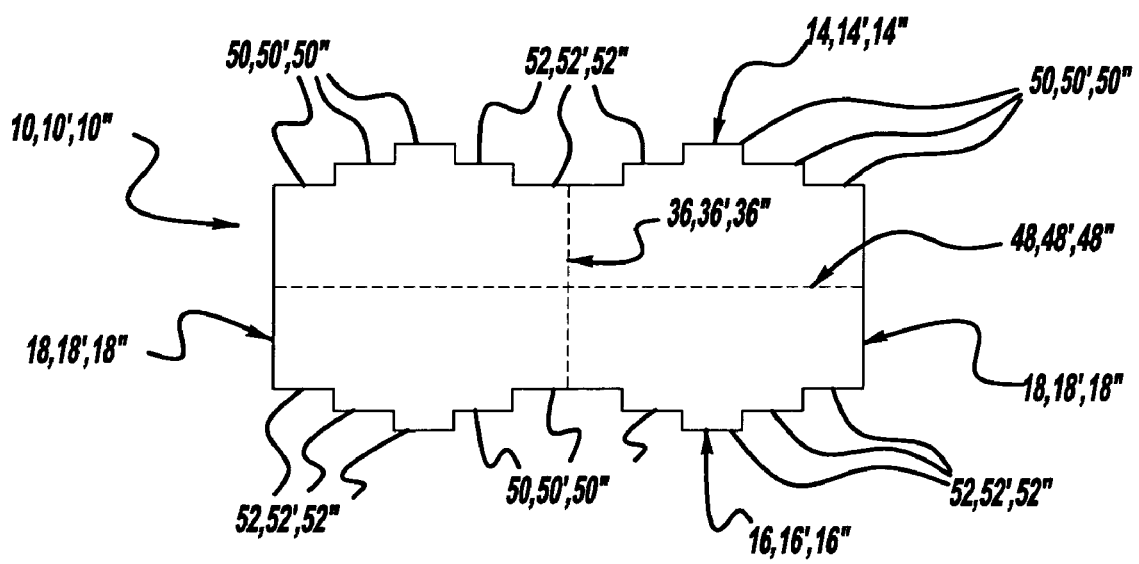
FIG. 8 is a cross-sectional view of an embodiment of an implant showing concentric cuts tiered upwards from an outer wall and tiered downwards toward a center of the implant body.
Figure 9:
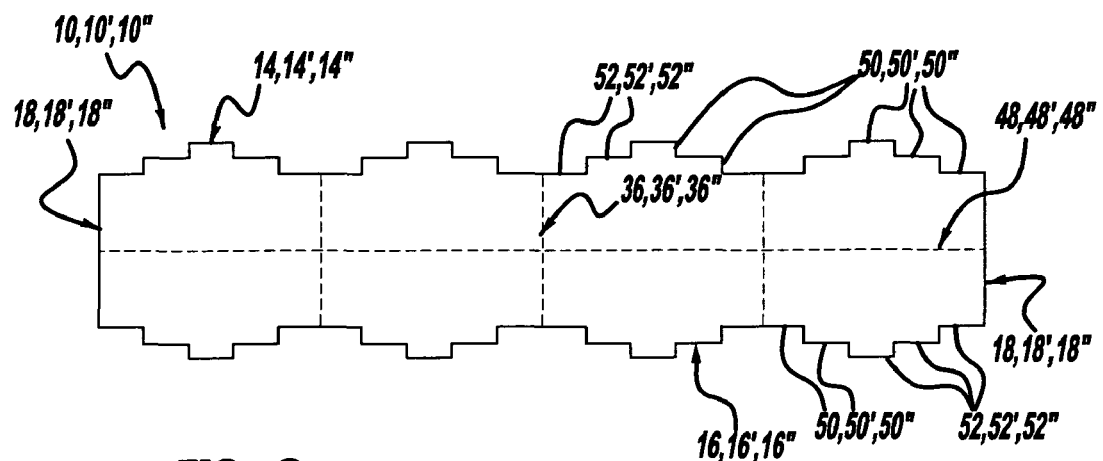
FIG. 9 is a cross-sectional view of an embodiment of an implant showing concentric cuts repeatedly tiered upwards from an outer wall and tiered downwards toward a center of the implant body.

As shown in FIG. 8, the tiered concentric cuts 42, 42', 42" can be tiered in different directions. Using a central axis 48, 48', 48" as a reference point, on the superior end face 14, 14', 14", there are upward tiered concentric cuts 50, 50', 50" starting from the outer sidewall 18, 18', 18", and then downward tiered concentric cuts 52, 52', 52" extending to the center 36, 36', 36" of the bone implant body 12, 12', 12". On the inferior end face 16, 16', 16", there are downward tiered concentric cuts 52, 52', 52" starting from the outer sidewall 18, 18', 18", and then upward tiered concentric cuts 50, 50', 50" extending to the center 36, 36', 36". This is only one example of arranging the tiered concentric cuts 42, 42', 42" and any other suitable tiering arrangement can be used. Furthermore, as shown in FIG. 9, the tiered concentric cuts 42, 42', 42" can be tiered in different directions repeatedly. This is accomplished by alternating upward tiered concentric cuts 50, 50', 50" and downward tiered concentric cuts 52, 52', 52" on both the superior end face 14, 14', 14" and the inferior end face 16, 16', 16". The concentric cuts 32' and tiered concentric cuts 42, 42', 42" aid in slip prevention to maintain the position of the bone implant 10, 10', 10" between adjacent vertebrae.

Figure 10:
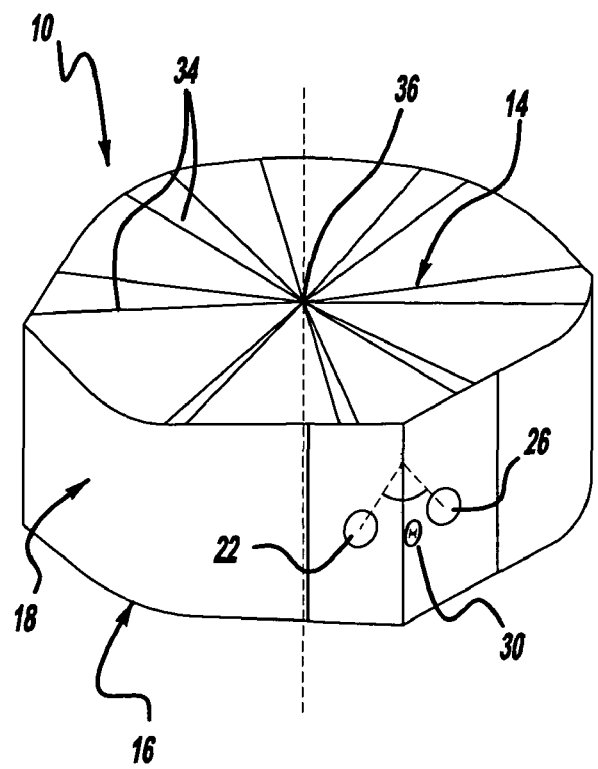
FIG. 10 is a perspective view of a first embodiment of an implant showing radial cuts on a superior surface and inferior surface of the implant body.
Figure 11:
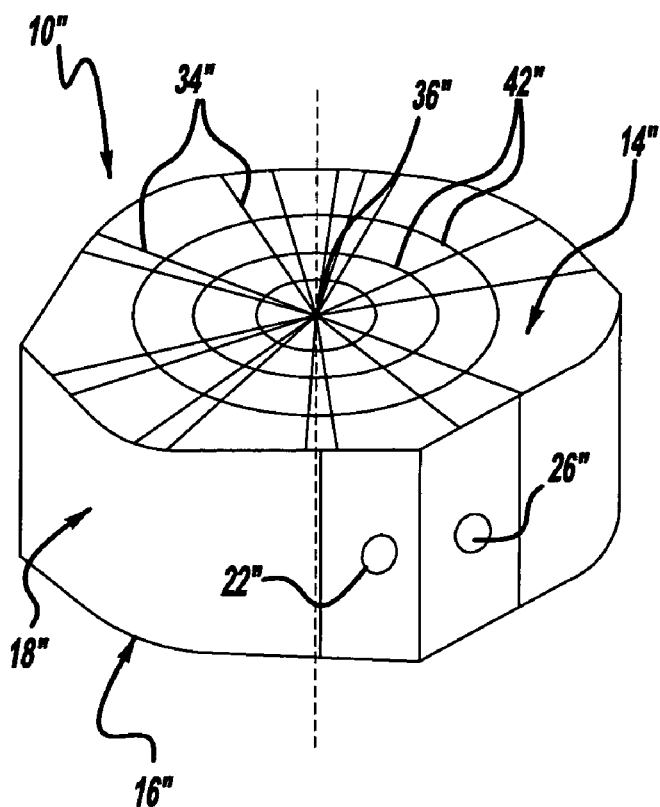
FIG. 11 is a perspective view of a third embodiment of an implant showing radial cuts and concentric cuts.
Figure 12:
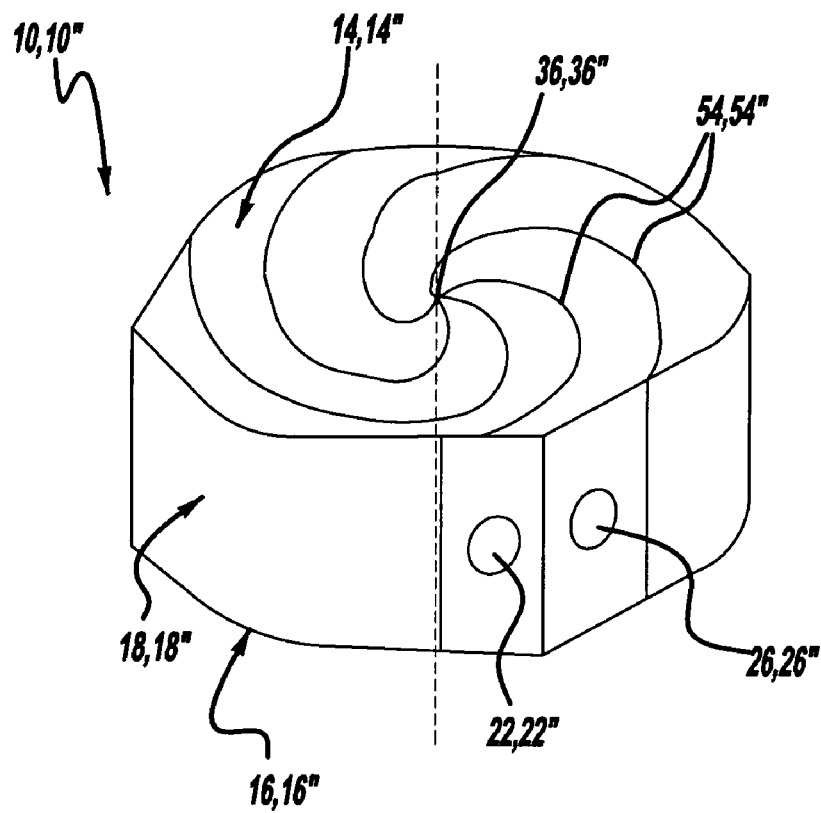
FIG. 12 is a perspective view of a first and third embodiments of an implant showing curved radial cuts on a superior surface and inferior surface of the implant body.

Another type of cut that the bone implant 10, 10" can include on the superior end face 14, 14" and the inferior end face 16, 16" is a radial cut 34, 34" in accordance with the third embodiment of the invention as shown in FIG. 3, and also as shown in FIG. 10 of the first embodiment, and on FIG. 11 of the third embodiment. The radial cuts 34, 34" extend radially from the center 36, 36" the outer sidewall 18, 18" of the bone implant body 12, 12". Each radial cut 34, 34" can be the same size, or alternatively, they can be different sizes. The radial cuts 34, 34" can be the only cuts on the bone implant body 12, 12" as in FIG. 10, or they can be applied along with any of the tiered concentric cuts 42, 42" described above, with one example shown in FIG. 11. Furthermore, the radial cuts 34, 34" can be curved radial cuts 54, 54" as shown in FIG. 12. These radial cuts 34, 34" can be made by cutting the bone implant 10, 10" with cutting means similar to those used to cut the tiered concentric cuts 42, 42", or by any other suitable means. The radial cuts 34, 34" are useful in slip prevention of the bone implant 10, 10" so that the bone implant 10' 10" does not shift positions when inserted between adjacent vertebrae.

The outer sidewall 18, 18', 18", 18''' extends between the superior end face 14, 14', 14", 14''' and the inferior end face 16, 16', 16", 16'''. Preferably, the outer sidewall 18, 18', 18", 18''' is in a circular shape. Alternatively, the outer sidewall 18, 18', 18", 18''' can be cut to any desired shape by cutting methods known in the art, or it can be left in the natural shape of a bone of an allograft. Preferably, the outer sidewall 18, 18', 18", 18''' includes, in general, two flat sidewall portions 20, 20', 20", 20'''. These flat sidewall portions 20, 20', 20", 20''' assist in making the gripping of the bone implant 10, 10', 10", 10''' by an implant insertion device 60 more secure. Additional flat sidewall portions can be included. The first flat sidewall portion 24, 24', 24", 24''' is preferably adjacent to a second flat sidewall portion 28, 28', 28", 28''', as shown for example in the first embodiment in FIG. 1.

A first insertion pin hole 22, 22', 22", 22''' is located on the first flat sidewall portion 24, 24', 24", 24''', extending from the outer sidewall 18, 18', 18", 18''' towards the center 36, 36', 36", 36''' of the bone implant body 12, 12', 12", 12'''. A second insertion pin hole 26, 26', 26", 26''' is located on the second flat sidewall portion 28, 28', 28", 28''', extending from the outer sidewall 18, 18', 18", 18''' towards the center 36, 36', 36", 36''' of the bone implant body 12, 12', 12", 12'''. The insertion pin holes 22, 22', 22", 22''' and 26, 26', 26", 26''' can extend completely to the center 36, 36', 36", 36''', or they can extend partially to the center 36, 36', 36", 36'''. Preferably, they extend a suitable distance to fit a movable pin 70 and a fixed pin 72 of an implant insertion device 60 so that the insertion-pins fit flushly in the insertion pin holes 22, 22', 22", 22''' and 26, 26', 26", 26'''.

The insertion pin holes 22, 22', 22", 22''' and 26, 26', 26", 26''' are preferably located at the same height on the flat sidewall portions 20, 20', 20", 20''' and are preferably located centrally with respect to the width of the flat sidewall portions 20, 20', 20", 20'''. The insertion pin holes 22, 22', 22", 22''' and 26, 26', 26", 26''' can be located at any other suitable location on the first and second flat sidewall portions 24, 24', 24", 24''' and 28, 28', 28", 28''' so as to accommodate an implant insertion device 60. In the first embodiment of the bone implant 10, the angle theta 30 between the first insertion pin hole 22 and the second insertion pin hole 26 is about 30 degrees, as shown in FIG. 1. Any other suitable angle theta 30, 30', 30", 30''' can be used, so long as the implant insertion device 60 can attach appropriately to the bone implant 10, 10', 10", 10'''. A boring tool or any other methods known in the art can be used to create the insertion pin holes 22, 22', 22", 22''' and 26, 26', 26", 26'''. Preferably, the first insertion pin hole 22, 22', 22", 22''' has a first inside pin surface 55, 55', 55", 55''' that is smooth. Preferably, the second insertion pin hole 26, 26', 26", 26''' has a second inside pin surface 56, 56', 56", 56''' that is smooth. The insertion pin holes 22, 22', 22", 22''' and 26, 26', 26", 26''' can each include an inner counter bore cut 38, 38', 38", 38''', as shown in FIGS. 4, 6, and 13. The counter bore cuts 38, 38', 38", 38''' are preferably located near the edge of the insertion pin holes 22, 22', 22", 22''' and 26, 26', 26", 26''', but they can be situated further back. The counter bore cuts 38, 38', 38", 38''' relieve stress from the insertion pin holes 22, 22', 22", 22''' and 26, 26', 26", 26''' applied by the insertion of a movable pin 70 and fixed pin 72. They are designed to reduce the stress concentration on the implant when the implant insertion device 60 is handling the bone implant 10, 10', 10", 10'''. They also aid in the prevention of chipping the bone implant 10, 10', 10", 10''' near the insertion pin holes 22, 22', 22", 22''' and 26, 26', 26", 26''' when inserting the pins 72 and 70 of the implant insertion device 60.

The bone implant 10, 10', 10" can further include an inner sidewall 57, 57', 57" extending between the superior end face 14, 14', 14" and the inferior end face 16, 16', 16" to define a hollow core 58, 58', 58", as shown in FIGS. 6 and 13. The hollow core 58, 58', 58" can be made using cutting methods known in the art in order to produce the dimensions desired. Alternatively, the hollow core 58, 58', 58" can be a hole occurring naturally in a donor allograft that can be further altered by machining if desired. The hollow core 58, 58', 58" is useful for adding bone grafting materials to the bone implant 10, 10', 10" to aid in fusion between the vertebrae.

One method of forming a bone implant 10, 10', 10" is by cutting concentric cuts 32' or tiered concentric cuts 42, 42" into the superior end face 14, 14', 14" and the inferior end face 16, 16', 16" of the bone implant 10, 10', 10". Any cutting means known in the art can be used. The bone implant 10, 10', 10" can be pre-formed to the desired shape before cutting the concentric cuts 32' or the tiered concentric cuts 42, 42".

Another method of forming a bone implant 10, 10" is accomplished by cutting radial cuts 34, 34" into the superior end face 14, 14" and the inferior end face 16, 16" of the bone implant 10, 10". This is also performed by using any cutting means known in the art. The bone implant 10, 10" can be preformed in the desired shape before cutting the radial cuts 34, 34".

Yet another method of forming a bone implant 10, 10" is accomplished by cutting concentric cuts 32, 32" into the superior end face 14, 14" and the inferior end face 16, 16" of the bone implant 10, 10", and then cutting radial cuts 34, 34" into the superior end face 14, 14" and the inferior end face 16, 16" of the bone implant 10, 10". Any cutting means known in the art can be used. Alternatively, the radial cuts 34, 34" can be cut first and then the concentric cuts 32, 32" can be cut second. Tiered concentric cuts 42, 42" can be cut instead of the concentric cuts 32, 32".

An implant insertion device 60 of the present invention is shown generally in FIG. 14. The implant insertion device 60 includes a handle 62, an insertion rod 64 that is attached to the handle 62, and an implant gripper 66 attached to the insertion rod 64. The implant gripper 66 includes a gripping surface 68. A movable pin 70 and a fixed pin 72 are located on and extending from the gripping surface 68. Also included is a pin actuator 74 for moving the movable pin 70 between an extended position and a retracted position relative to the gripping surface 68.

The implant insertion device 60 is preferably made from biocompatible materials so as to not cause inflammation or reactions when exposed to a patient's tissue. The purpose of the implant insertion device 60 is to guide a bone implant 10, 10', 10", 10''' to an implantation site in a patient's body and deposit the bone implant 10, 10', 10", 10''' in the implantation site. It is ideal that the implant insertion device 60 have minimal projections from it so as not to cut into tissue unnecessarily when guiding a bone implant 10, 10', 10", 10''' to the site of insertion. The handle 62 is of a sufficient size so that a surgeon or person operating the implant insertion device 60 can hold it firmly and be able to manipulate the implant insertion device 60 with ease. The insertion rod 64, attached to the handle 62, is sized so that it can effectively reach the site of insertion while maintaining a small diameter in order to move efficiently and as non-invasively as possible through the tissue of the patient.

The implant gripper 66 can be removably attached to the insertion rod 64 so that different size implant grippers 66 can be interchanged. This is advantageous because the same insertion instrument can be used for different size implants, thus reducing the number of instruments that a surgeon needs to have. The implant gripper 66 has a gripping surface 68 and is used to grip the bone implant 10, 10', 10", 10'''. Preferably, the gripping surface 68 is in the form of a v-shape to accommodate and effectively abut the flat sidewall portions 20, 20', 20", 20''' of the bone implant 10, 10', 10", 10''', as shown in FIGS. 15 and 16. Other shapes can be used that suitably accommodate the bone implant 10, 10', 10", 10'''. The gripping surface 68 can be smooth, or have any other suitable texture to aid in securing the bone implant 10, 10', 10, 10'''.

On the gripping surface, the movable pin 70 and the fixed pin 72 are shown in further detail in FIG. 15. Preferably, the movable pin 70 and the fixed pin 72 make an angle phi 76 of about 30 degrees. This angle phi 76 is in accordance with the angle theta 30 of about 30 degrees of the first embodiment of the implant 10 so that the movable pin 70 and the fixed pin 72 fit flushly inside the insertion pin holes 22 and 26. Any other suitable angle phi 76 can be used as long as the pins 70 and 72 are situated to fit inside the insertion pin holes 22, 22', 22", 22''' and 26, 26', 26", 26'''. Preferably, the pins 70 and 72 can be smooth to fit into smooth insertion pin holes 22, 22', 22", 22''' and 26, 26', 26", 26''', or alternatively, they can be textured. The pins 70 and 72 are of a length suitable to fit securely inside the insertion pin holes 22, 22', 22", 22''' and 26, 26', 26", 26'''. Further detail in FIG. 16 and FIG. 17 shows that the fixed pin 72 is situated in a fixed pin slot 78, and the movable pin 70 is disposed inside a movable pin slot 80. The pin slots 78 and 80 can be formed by any cutting means known in the art, or alternatively, they can be formed in the insertion device 60 as part of a mold.

The movable pin slot 80 is connected to a pin driving shaft 82 as shown in FIGS. 15 and 16. The pin driving shaft 82 runs a length extending down the insertion rod 64, and the pin driving shaft 82 can extend into the handle 62 as well. The pin driving shaft 82 is sized to accommodate a pin driver 84. The pin driver 84 can be attached to the movable pin 70 in order to drive the movable pin 70 into a insertion pin hole 26, 26', 26", 26'''. The pin driver 84 can alternatively be moved and attached to the movable pin 70 so that the gripper 66 can be interchanged.

The movable pin 70 is moved into the insertion pin hole 26, 26', 26", 26''' by activating a pin actuator 74, shown in FIG. 14. The pin actuator 74 can be in the form of a finger operated switch. Alternatively, the pin actuator 74 can be in any other suitable form. The pin actuator 74 is preferably located on the insertion rod 64, but alternatively, it can be located on the handle 62. Activating the pin actuator 74 causes the pin driver 84 to drive the movable pin 70 into the insertion pin hole 26, 26', 26", 26'''. The movable pin 70 can be locked in place with a lock 86 to ensure that it does not exit the insertion pin hole 26, 26', 26", 26''' while inserting the bone implant 10, 10', 10", 10''' in a spinal column. The movable pin 70 can then be unlocked when it is desired to remove the movable pin from the bone implant 10, 10', 10", 10'''. The lock 86 can be located on the insertion rod 64 or on the handle 62. The lock 86 can take the form of a finger operated switch, or any other suitable locking mechanism.

Figure 19:
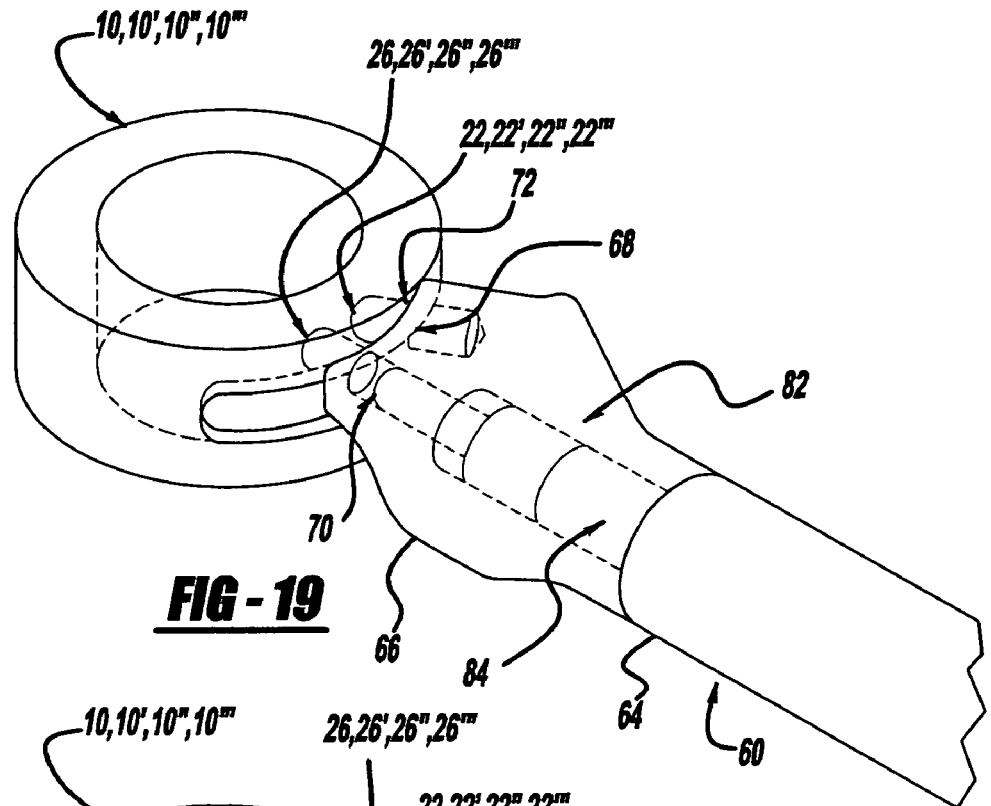
FIG. 19 is a close-up view of the present invention of a implant gripper of an implant insertion device showing a first step in attaching an implant to the device.
Figure 20:
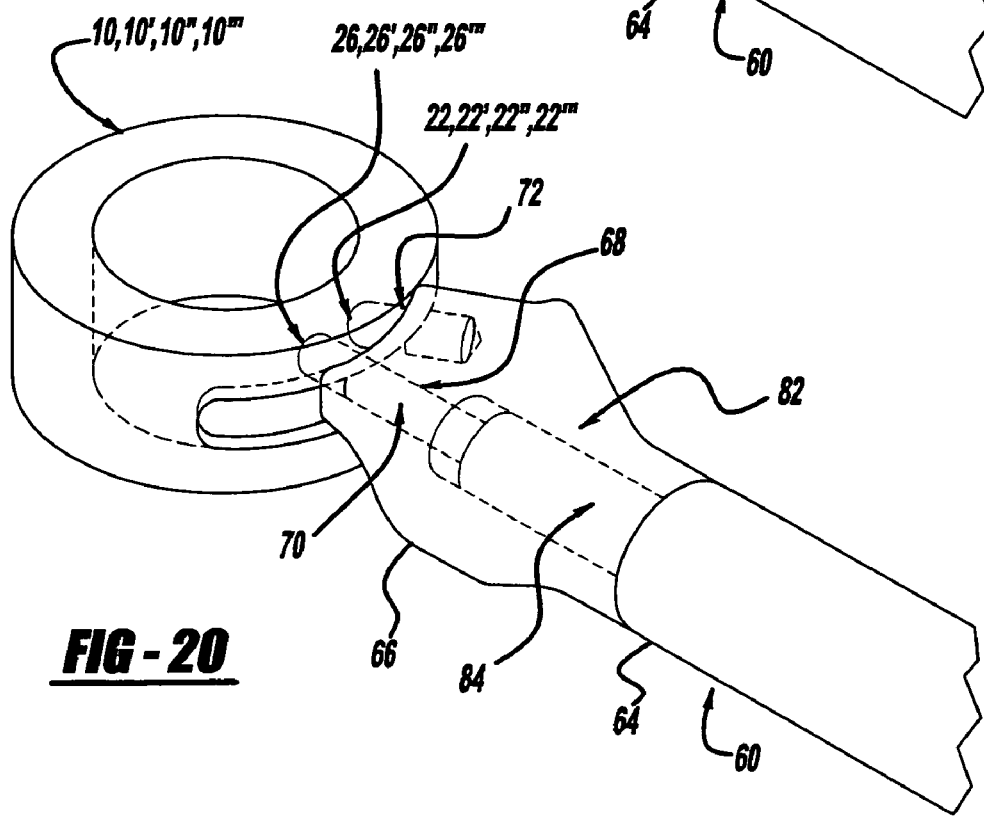
FIG. 20 is a close-up view of the present invention of an implant gripper of an implant insertion device showing a second step in attaching an implant to the device.

FIG. 18 shows a bone implant 10, 10', 10", 10''' attached to an implant insertion device 60. A method of attaching a bone implant 10, 10', 10", 10''' to the implant insertion device is accomplished by first inserting a fixed pin 72 on the implant gripper 66 into the first insertion pin hole 22, 22', 22", 22''' of the bone implant 10, 10', 10", 10''' as shown in STEP 1 of FIG. 19. The movable pin 70 is situated so that it is lined up with the second insertion pin hole 26, 26', 26", 26'''. Next, as shown in STEP 2 of FIG. 20, the movable pin 70 is driven into the second insertion pin hole 26, 26', 26", 26''' by activating the pin actuator 74.

A method of detaching a bone implant 10, 10', 10", 10''' from the implant insertion device is accomplished by the reversal of the steps in the method of attaching the bone implant 10, 10', 10", 10'''. First, the movable pin 70 is detached from the second insertion pin hole 26, 26', 26", 26''' by activating the pin actuator 74 to drive the movable pin 70 back into the implant gripper 66. The second step is to detach the fixed pin 72 on the implant gripper 66 from the first insertion pin hole 22, 22', 22", 22'". The fixed pin 72 can be simply pulled out of the first insertion pin hole 22, 22', 22", 22'", or can be detached in any other suitable way.

A method of inserting a bone implant 10, 10', 10", 10'" with an implant insertion device 60 is accomplished by first attaching the bone implant 10, 10', 10", 10'" to the implant insertion device 60 by the method described above. Next, the bone implant 10, 10', 10", 10'" is inserted into a spinal column in a patient and guided to a site of insertion. The bone implant 10, 10', 10", 10'" can be inserted from an oblique lateral direction so that the bone implant 10, 10', 10", 10'" can fuse between discs L5 and S1. Alternatively, the bone implant 10, 10', 10", 10'" can be inserted from a straight anterior direction so that the bone implant 10, 10', 10", 10'" can fuse between discs L4 and L5. Finally, the bone implant 10, 10', 10", 10'" is detached from the implant insertion device 60 by the method described above.

Throughout this application various patents are referenced by number. The disclosures of these patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. An implant insertion device comprising:
   an insertion rod having a longitudinal axis; and
   an implant gripper attached to said insertion rod, said implant gripper including:
   a v-shaped gripping surface intersecting the longitudinal axis of the insertion rod;
   a first pin extending from and fixed relative to said v-shaped gripping surface; and
   a second pin extending through and movable relative to said v-shaped gripping surface between a first position wherein the second pin extends from the v-shaped gripping surface a distance x and a second position wherein the second pin extends a distance less than x from the v-shaped gripping surface,
   wherein said first pin and said second pin are offset on said v-shaped gripping surface and extend in a non-parallel manner.

2. The insertion device of claim 1, wherein said first pin and said second pin are offset on said gripping surface by an angle of approximately 30 degrees.

3. The insertion device of claim 1, wherein said first pin and said second pin are smooth.

4. The insertion device of claim 1, wherein said implant gripper is removable from said insertion rod.

5. A method of engaging an implant with an implant insertion device according to claim 1, comprising the steps of:
   (a) retracting the second pin relative to the gripping surface of the implant insertion device;
   (b) positioning the implant adjacent to the gripping surface such that the first pin extending from the gripping surface extends into an insertion pin hole of the implant; and
   (c) extending the second pin relative to the gripping surface such that the second pin extends into a second insertion pin hole of the implant, thereby effectively reversibly locking the implant onto said device.

6. The method of claim 5 further comprising the step of
   (a) retracting the second pin of the implant gripper from the insertion pin hole of the implant; and
   (b) moving the gripping surface away from the implant such that the first pin is removed from the second insertion pin hole of the implant and the implant insertion device is disengaged from the implant device.

7. A method of insertion of an implant with an implant insertion device according to claim 1, comprising the steps of:
   (a) attaching the implant to the implant insertion device by retracting the second pin relative to the gripping surface of the implant insertion device; positioning the implant adjacent to the gripping surface such that the first pin extending from the gripping surface extends into an insertion pin hole of the implant, and extending the second pin relative to the gripping surface such that the second pin extends into a second insertion pin hole of the implant;
   (b) inserting said implant in a spinal column; and
   (c) detaching said implant from said implant insertion device by retracting said second pin from said second insertion pin hole of said implant, and detaching said first pin of said implant gripper from said insertion pin hole of the implant.

8. An implant insertion assembly comprising:
   an implant insertion device according to claim 1; and
   an implant comprising an outer sidewall which defines one or more insertion pin holes configured to receive the first and second pins.

9. The assembly according to claim 8, wherein said insertion pin holes include a counter bore cut.

10. The assembly according to claim 8, wherein the implant outer sidewall includes at least two flat sidewall portions and first and second insertion pin holes are defined along the respective flat sidewall portions.

11. The assembly according to claim 8, wherein said implant includes a superior end face and an inferior end face and one or both of said superior end face and said inferior end face include a plurality of radial cuts.

12. The assembly according to claim 11, wherein said plurality of radial cuts are tiered.

13. The assembly according to claim 8, wherein said implant includes a superior end face and an inferior end face and one or both of said superior end face and said inferior end face include a plurality of concentric cuts.

14. The assembly according to claim 13, wherein said plurality of concentric cuts are tiered.

15. The assembly according to claim 8, wherein said implant includes a superior end face and an inferior end face and one or both of said superior end face and said inferior end face include a plurality of concentric cuts and a plurality of radial cuts.

16. The assembly according to claim 8, wherein said implant defines a hollow core.

17. The assembly according to claim 8, wherein said implant is a biocompatible material.

18. The assembly according to claim 8, wherein said implant insertion device is a biocompatible material.

19. An implant insertion device comprising:
   an insertion rod having a longitudinal axis; and
   an implant gripper extending from said insertion rod, said implant gripper including:
   a v-shaped implant gripping surface intersecting the longitudinal axis of the insertion rod;

a first pin on and fixed relative to said v-shaped implant gripping surface; and a second pin extending through and movable relative to said v-shaped implant gripping surface, said second pin being substantially aligned with said longitudinal axis of said insertion rod and non-parallel to said first pin.

20. An implant insertion device comprising:

a handle having a gripping surface;

an insertion rod extending from said handle, said insertion rod defining a longitudinal axis;

an implant gripper extending from said insertion rod, said implant gripper including:

a v-shaped implant gripping surface intersecting the longitudinal axis of the insertion rod;

a first pin on and fixed relative to said v-shaped implant gripping surface; and a second pin extending through and movable relative to said v-shaped implant gripping surface, said second pin being substantially aligned with said longitudinal axis of said insertion rod and non-parallel to said first pin; and an actuator positioned proximal to said handle for moving the second pin relative to said v-shaped implant gripping surface.

* * * * *